US011266761B2

(12) United States Patent
Hogg-Cornejo et al.

(10) Patent No.: US 11,266,761 B2
(45) Date of Patent: Mar. 8, 2022

(54) SYSTEM FOR FORMING A RIGID SUPPORT

(71) Applicant: Cast21, Inc., Chicago, IL (US)

(72) Inventors: Veronica Andrea Hogg-Cornejo, Denver, CO (US); Abhilash Seshadri, Chicago, IL (US); Ashley Sue Moy, Chicago, IL (US); Yaser Kazmi, Chicago, IL (US); Virendra Desai Patil, Chicago, IL (US); Ethan Wisniewski, Gurnee, IL (US); Brittany Lung, Seattle, WA (US); Andrew Steveson, Champaign, IL (US); Jason Troutner, Columbus, OH (US); Adrian Choy, Chicago, IL (US)

(73) Assignee: Cast21, Inc., Chicago, IL (US)

( * ) Notice: Subject to any disclaimer, the term of this patent is extended or adjusted under 35 U.S.C. 154(b) by 724 days.

(21) Appl. No.: 16/183,823

(22) Filed: Nov. 8, 2018

(65) Prior Publication Data
US 2019/0105423 A1 Apr. 11, 2019

Related U.S. Application Data

(63) Continuation-in-part of application No. 15/717,069, filed on Sep. 27, 2017, now abandoned.
(Continued)

(51) Int. Cl.
*A61F 5/058* (2006.01)
*A61F 13/04* (2006.01)
(Continued)

(52) U.S. Cl.
CPC .............. *A61L 15/14* (2013.01); *A61F 5/058* (2013.01); *A61F 5/05841* (2013.01);
(Continued)

(58) Field of Classification Search
CPC .... A61F 5/0104; A61F 5/0106; A61F 5/0109; A61F 5/0111; A61F 5/0118; A61F 5/04;
(Continued)

(56) References Cited

U.S. PATENT DOCUMENTS 3,631,854 A * 1/1972 Fryer ...................... A61F 13/04
602/8
4,273,115 A 6/1981 Holland et al.
(Continued)

FOREIGN PATENT DOCUMENTS

DE 102005058243 6/2007
EP 0397998 A1 11/1990
(Continued)

OTHER PUBLICATIONS

Bioengineering News, Oct. 6, 2016 Perfectly Cast; www.asme.org/engineering-topics/articles/bioengineering/perfectly-cast.
(Continued)

Primary Examiner — Keri J Nelson
(74) Attorney, Agent, or Firm — McDonnell Boehnen Hulbert & Berghoff LLP

(57) ABSTRACT

The system invention describes a support and improved method of application and removal. The support, comprised of a network of flexible, non-porous, multi-lumen tubing interlaces at a plurality of junctions to form a lattice structure. Apertures designed to accommodate boney prominences also permit air or water to reach the skin underneath and encourage rapid fluid flow internally through the lattice. A hydrophobic, thermal-resistant, flowable padding layer is injected within a secondary lumen to the lattice structure, spanning its complete surface area. As a result, the breathability of the support is not affected by this padding layer because it mirrors the apertures of the lattice. At least one liquid is injected into the structure and configured to trans-
(Continued)

form into a solid when acted on by an external mechanical stimulus.

17 Claims, 20 Drawing Sheets

Related U.S. Application Data

(60) Provisional application No. 62/429,953, filed on Dec. 5, 2016, provisional application No. 62/586,495, filed on Nov. 15, 2017, provisional application No. 62/672,081, filed on May 16, 2018.

(51) Int. Cl.
*A61L 15/07* (2006.01)
*A61L 15/14* (2006.01)
*A61L 15/12* (2006.01)

(52) U.S. Cl.
CPC .......... *A61F 5/05866* (2013.01); *A61F 13/04* (2013.01); *A61L 15/07* (2013.01); *A61L 15/12* (2013.01)

(58) Field of Classification Search
CPC ........ A61F 5/05; A61F 5/058; A61F 5/05841; A61F 5/05866; A61F 13/04; A61L 15/07; A61L 15/12; A61L 15/14
See application file for complete search history.

(56) References Cited

U.S. PATENT DOCUMENTS

| | | | |
|---|---|---|---|
| 4,427,002 A | 1/1984 | Baron et al. | |
| 4,483,332 A | 11/1984 | Rind | |
| 4,498,467 A | 2/1985 | Kirkpatrick et al. | |
| 4,766,890 A | 8/1988 | Hoorah | |
| 4,817,590 A * | 4/1989 | Stancik, Jr. ............. | A61F 13/04 128/DIG. 20 |
| 5,088,484 A | 2/1992 | Freeman | |
| 5,725,487 A | 3/1998 | Freeman | |
| 5,836,902 A | 11/1998 | Gray | |
| 5,857,987 A | 1/1999 | Habermeyer | |
| 6,547,751 B1 | 4/2003 | Barberio | |
| 6,613,006 B1 | 9/2003 | Asherman | |
| 6,942,628 B1 | 9/2005 | Watson | |
| 7,037,283 B2 | 5/2006 | Karason | |
| 7,767,874 B2 | 8/2010 | Kellogg | |
| 7,883,490 B2 * | 2/2011 | Casey, II ............. | A61M 5/284 604/82 |
| 7,985,192 B2 | 7/2011 | Sheehan | |
| 8,381,903 B2 * | 2/2013 | Ilfrey ................. | B65D 81/3266 206/219 |
| 8,608,676 B2 | 12/2013 | Jorissen | |
| 8,672,864 B2 | 3/2014 | Nordt, III | |
| 9,770,358 B2 | 9/2017 | Evans et al. | |
| 2006/0282030 A1 | 12/2006 | Martin | |
| 2007/0016323 A1 | 1/2007 | Fried | |
| 2008/0125688 A1 | 5/2008 | Kellogg | |
| 2010/0069803 A1 | 3/2010 | Linares | |
| 2011/0132782 A1 | 6/2011 | Ilfrey | |
| 2013/0035620 A1 | 2/2013 | Schütz et al. | |
| 2013/0053740 A1 | 2/2013 | Mustafa | |
| 2015/0230961 A1 | 8/2015 | McGuckin | |
| 2015/0282975 A1 | 10/2015 | Herzman | |

FOREIGN PATENT DOCUMENTS

| | | |
|---|---|---|
| GB | 2490709 A | 11/2012 |
| JP | 5-309110 | 11/1993 |
| WO | 2010099130 A1 | 9/2010 |
| WO | 2015157648 | 10/2015 |

OTHER PUBLICATIONS

University of Illinois at Urbana-Champaign; Jan. 4, 2016 Student Team Develops New Way of Treating Broken Bones; www.odtmag.com/contents/view_breaking-news/2016-01-04/student-team-develops-new-way-of-treating-broken-bones.
MedGadget; Jul. 1, 2013; Cortex 3D-Printed Cast Improves Comfort and Reduces Waste, Scott Jung; www.medgadget.com.
Materialise; May 27, 2016; Designing a Patient-Specific 3D-Printed Cast With the Lightweight Structures Modules, Todd Pietila; materialise.com.
Fastcodeisng; Apr. 28, 2014; Could Thid 3-D Printed Cast Really Heal Bones Faster?, Carey Dunne; www.fastcodesign.com/3029766/could-this-e-d-printed-cast-really-heal-bones-faster.
Russian Company Looks to Bring 3D Printed Casts to Market, Feb. 7, 2015, Whitney Hipolite; 3dprint.com/43103/3d-printed-cast.
Final Rejection USPTO Jul. 10, 2018 Parent U.S. Appl. No. 15/717,069.
Non Final Rejection USPTO Nov. 30, 2017 Parent U.S. Appl. No. 15/717,069.
PCT/US2018/059929 Written Opinion; dated Feb. 20, 2019.

* cited by examiner

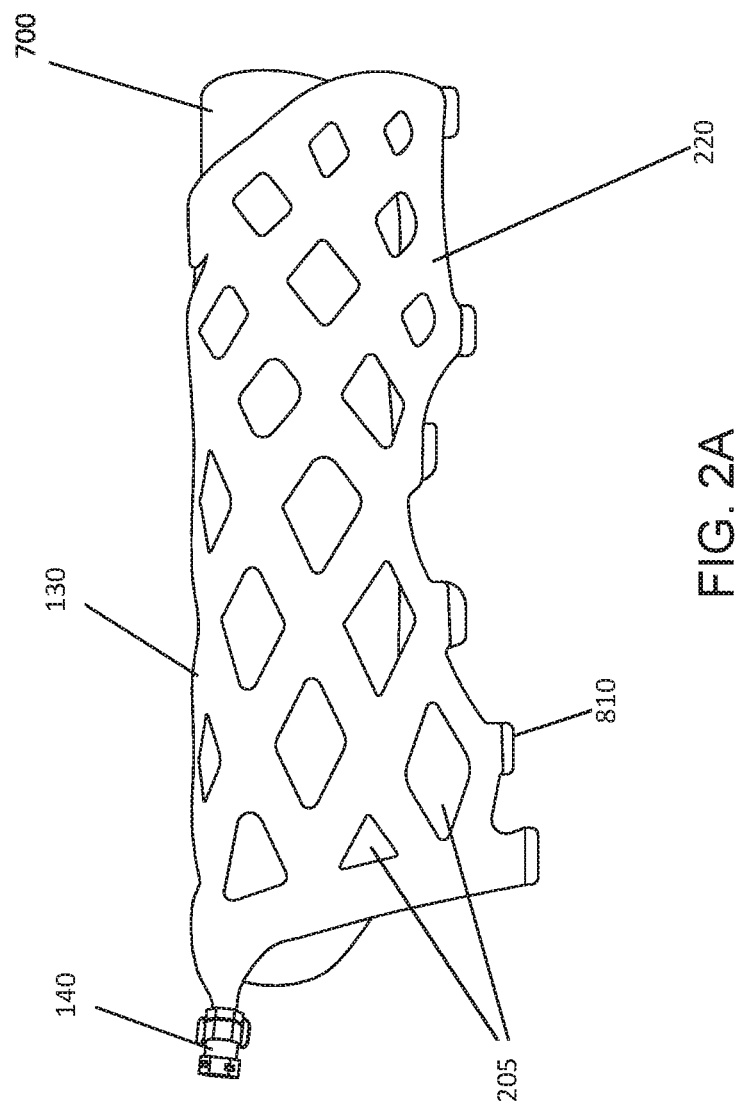

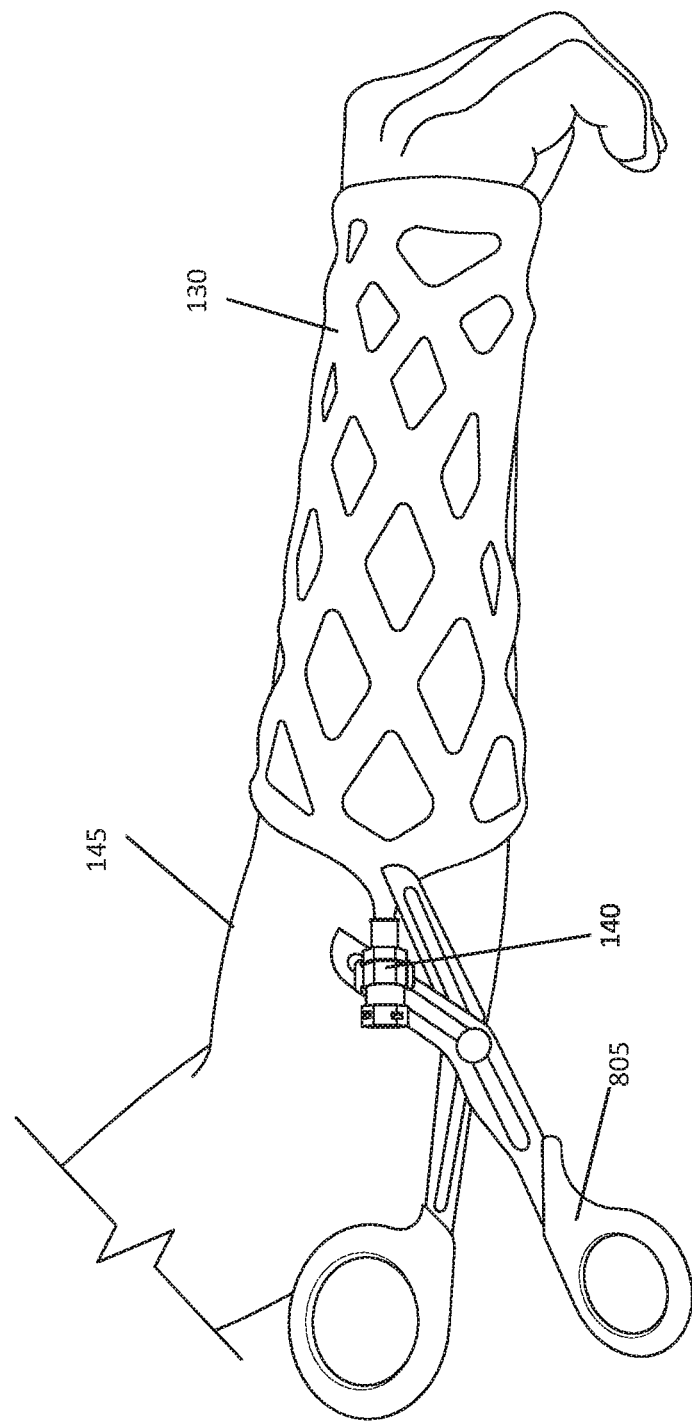

SYSTEM FOR FORMING A RIGID SUPPORT

CROSS REFERENCE TO RELATED APPLICATIONS

The present system invention in a Continuation In Part of U.S. application Ser. No. 15/717,069 filed Sep. 27, 2017, which claims priority to U.S. Provisional Application No. 62/429,953 filed Dec. 5, 2016. This application also claims priority to U.S. Provisional Application No. 62/586,495 filed Nov. 15, 2017 and U.S. Provisional Application No. 62/672,081 filed May 16, 2018. All referenced applications are hereby incorporated by reference.

FIELD OF THE INVENTION

The system invention relates to orthotics and orthopedic supports such as casts, braces, and splints; specifically, for the immobilization of a joint and limb; referred to herein generally as a support.

BACKGROUND OF THE INVENTION

Standard supports are made of fiberglass or plaster with an underlying cotton padding that is in direct contact with the skin. These supports fully encase the limb, which in turn makes the product cumbersome, heavy, and impermeable. The closed, rigid structure and absorbent cotton layer underneath have been known to trap water, sweat, heat, and bacteria that cause discomfort, odor, itchiness, and a higher risk of skin infection. Additionally, the limb being fully enclosed prevents direct examination, cleaning, and treatment of the affected body area.

The method of application for fiberglass and plaster supports requires auxiliary resources and a particular skill in the art that has proven problematic. Access to heated water is needed to initially soak the rolls of fiberglass or plaster just to make the material moldable and initiate the curing process. As the product is then wrapped around the limb, there is a limited window in which the material is soft enough to be workable, making the application process variable and highly dependent on the skills of the cast technician. Typically, the time required for these products to completely dry and reached their maximum strength can take up to 24-72 hrs. Additionally, the safe removal of these products requires expensive specialty equipment that is cumbersome to store. Oscillating cast saws are required to cut through the rigid structure and often release messy dust particles, are traumatic for younger patients due to the loud grinding noise created, and the higher potential for cutting or burning the patient's skin underneath. Moreover, as a result of the application and removal processes needed for standard casting, treatment is restricted to only those that have access to the auxiliary resources of heated water, electricity, and costly equipment, which in many regions of the world can be limited. To address these disadvantages, several new product innovations have come to market but have fallen short in providing an optimal solution for patient and providers alike.

Recently, 3D printing was introduced to construct waterproof and breathable supports in an attempt to eliminate the aforementioned problems of standard casting. Although these supports can be custom-built to each patient with the use of advanced 3D scanners, 3D printed casts fail to mediate issues of high costs, long turn-around times to reach the patient, or the need for additional specialized equipment to complete the application process. Moreover, patients have described these products as uncomfortable because the rigid support is in direct contact with the skin without a cushioning layer between.

Other supports utilize layering of materials to develop more comfortable and cost-friendly designs. U.S. Pat. No. 4,483,332 (1984) details an orthopedic support constructed by a network of tubing injected with at least one liquid, such that it hardens into a rigid support structure after an external stimulus is applied. Like 3D-printed casts, this method creates a waterproof and breathable support that can be molded to better fit the patient. The potential advantages of this method over 3D-printed casts includes reduced application time, lower overhead costs, and less patient discomfort. Even so, prior art using this technology has failed to eliminate the need for additional equipment or water to complete the application process. Furthermore, although many of the materials described are waterproof, few tackle the issue of bacterial growth and skin complications for the patient. Similar products using this method of construction fail to maintain the breathability of the lattice structure by adding a padding layer underneath obstructing the apertures. Therefore, there still exists a need for optimal design and simple handling of a product that mediates issues of increased risk of skin morbidities for the patient, slowed treatment processes, and overall patient dissatisfaction.

SUMMARY OF THE INVENTION

The system invention relates to orthotics and orthopedic supports such as casts, braces, and splints; specifically, for the immobilization of a joint and limb; referred to herein generally as a support. The system invention resolves many of the issues associated with standard casting, much of which prior art has failed to fully address. The described system permits rapid placement of the invention around the limb to create a custom fitting, breathable, lightweight, and waterproof rigid support that streamlines the treatment process for providers, reduces the risk of skin morbidities associated with standard casts, and improves the overall quality of life of patients throughout their rehabilitation.

The invention described in this document is a support and alternative system of application and removal to and from the affected body area. The preferred embodiment comprises of two primary components that fasten together to complete the system: 1) a flexible sleeve and 2) an external pack. All primary components of the system invention, as well as other embodiments to the system will be described.

The first system component, a flexible sleeve, is defined by a network of elastic tubing, configured to have at least one lumen. Layers of elastic material are stacked in a specific configuration of thicknesses to create a preferred multi-lumen embodiment that withstands high internal pressures and reduces kinking in the material. This network of tubing interlaces at a plurality of junctions to form a lattice structure. In a preferred embodiment, a thin elastic material that is nonporous and biocompatible is used to construct the network of tubing to make the apparatus waterproof and resistant to bacterial accumulation or tissue ingrowth of the patient's skin. Apertures specifically designed within the lattice pattern accommodate boney prominences, permit air or water to reach the skin underneath, and encourage rapid flow of liquid throughout its internal structure. The final configuration for the network of tubing varies according to the specific body area affected, as well as the differing support required to treat individual injuries. A hydrophobic flowable material can be injected into the lumen of the lattice structure that directly abuts the skin for cushioning. The padding must span the entire surface area of the flexible sleeve to act as a protective thermal-resistant layer. The breathability of the sleeve is not impeded by this padding layer. A valve is secured to at least one inlet of the network of tubing that connects to the external pack component of the system invention.

The second component of the system, an external pack, contains at least one liquid within its UV-resistant casing. The preferred embodiment of the external pack consists of an internally secured handle on an end opposing to an outlet. At least two frangible seals are located in parallel to create at least three chambers along the length of the external pack. At least one liquid, configured to transform into a solid when acted on by an external mechanical stimulus, is housed within the chambers of the external pack. Optional additives, such as colorants, are contained in at least one of the chambers separate from the other liquids. A valve secured in the outlet is used to connect with the flexible sleeve and permit fluid flow between components. A preferred method of use for the external pack utilizes the handle to roll the pack material toward the opposing valve. This process applies pressure to rupture through the most adjacent frangible seal and allow mixing of the liquids. Continued rolling of the pack toward the valve ruptures all additional frangible seals in parallel sequentially. The liquid contents of the external pack are preferably mixed by repeatedly inverting the pack prior to engaging the valves and injecting contents into the network of flexible tubing.

Quick coupling valves engage and lock the flexible lattice network to the external pack and facilitate two-way fluid flow. In the preferred application, all liquid contents in the external pack are transferred to the flexible lattice structure. The two-way flow of the valves also permits removal of excess air within the network of tubing that could potentially compromise the structural integrity of the final rigid support. After liquid transfer has been completed, a built-in shut-off feature of the valves prevents any spilling of liquids during disconnection. The external pack can then be disposed.

In the preferred application, the rapid injection of liquid into the flexible network of tubing provides a period in which the filled sleeve can be manually molded about the limb prior to fully curing into its rigid structure. An optional elastic bandage made of a thin and breathable material can be used to wrap around the limb to better conform the support. The elastic wrap allows for heat created from the curing of resin to dissipate. Sufficient curing of the support can occur within 10-15 minutes of initiating the application process, at which point the elastic wrap is removed and valve component of the support cut off with shears. Both items are then disposed.

In a preferred method of removing the support, clinical shears are used to cut through the tabs along the cutting seam avoiding all resinous material. The cast can then be manually spread open and removed from the affected area. The preferred process of removal eliminates the messy and bothersome production of dust particles caused using cast saws. The method also reduces the trauma of noisy and potentially harmful sawing can have on young patients.

An optional embodiment to the system invention includes a flexible measuring strip to appropriately size the support to the affected body area of the patient. For a short arm support model, the preferred method of use would require the measuring strip to be wrapped around the palm, followed by the forearm to check circumferences and properly select the support size for the patient. An additional embodiment for the short arm support model includes an optional plastic insert. The plastic insert concentrically lines the surface of the flexible sleeve and is in direct contact with the skin. The optional embodiment is removable and acts as a shape holder to assist sliding the limb through the lattice network. The plastic insert is then removed prior to initiating the mixing of the resinous liquids used fill the flexible sleeve. The plastic insert is not a permanent component to the system invention, rather an option for a temporary aide in the application process.

In the preferred embodiment, at least one liquid is defined to include a polyurethane resin, catalyst, and coloring agent, that when mixed together transform into a rigid structure in the form of the lattice structure. The final hardened resin is of a single homogenous color with a minimum Shore Hardness of at least 70D. Alternative variations of this embodiment include additives such as retardants or accelerants that alter the curing time of the hardenable liquid in order to vary the use of the system making it suitable for various applications.

In an alternative application, the hardenable liquids, defined to include a polyurethane resin and catalyst, are mixed thoroughly prior to the bursting of the final frangible seal separating the colorant. The resinous contents are not mixed further after the coloring agent has been introduced, but rather immediately injected into the network of tubing. This alternative application method creates a different coloring scheme in which a tie-dye effect is seen throughout entire lattice structure, rather than a single homogenous color. As provided, the colorant is typically a non-white pigment colorant that can be added. Since the resin and catalyst typically mix into a solid that is white in nature to change the coloring a non-white pigment would be added to the liquids.

A different embodiment of the flexible lattice network consists of a non-flowable thermal-resistant padding layer that is encased internally within the layers of the thin elastic tubing material. No adhesives are used to secure the padding to a surface of the lattice network, and the padding layer includes apertures that correspond to the flexible lattice network. In a preferred embodiment of this variation, the thermal-resistant padding material is closed-cell to prevent moisture absorption.

In yet another embodiment, the thermal-resistant padding layer may include an adhesive layer and secured the outer surface of the lattice structure that will be in direct contact with the skin. Preferably, the layer of adhesive and padding materials further includes apertures corresponding to the lattice structure apertures such that the flow of air and water to the body area is not impeded.

In an alternative embodiment, the non-flowable padding layer can be directly welded to the flexible sleeve and located internally between the thin elastic layers or externally to the lattice structure. In both variations of this embodiment, the apertures of the padding layer correspond to those of the flexible sleeve such that flow of air or water to the body area is not impeded.

The various embodiments or combination of embodiments to create a complete system invention provide a superior solution to prior art casts, braces, and splints. Numerous other advantages and features of the invention will become readily apparent from the following detailed description of the accompanying system drawings and claims.

BRIEF DESCRIPTION OF THE DRAWINGS

A fuller understanding of the foregoing system invention and method of application may be had by reference to the accompanying drawings, wherein:

FIG. 1b is a perspective view of an embodiment of the final rigid support constructed from the system invention in FIG. 1a;

FIG. 2a is a side view an embodiment of the flexible sleeve referenced in FIG. 1a including temporary and optional components to the system invention;

FIG. 7b shows an optional component to be used with the valves illustrated in FIG. 7a;

FIG. 8 is a perspective view of one aspect of the system in which the valve component is being removed after use;

DETAILED DESCRIPTION OF THE EMBODIMENTS

While the system invention is susceptible to embodiments of varying forms, shown are drawings of the preferred embodiments of the present system invention and method for using the same will be detailed herein. However, it should be understood that the present disclosure is an exemplification of the principles of the invention and not intended to limit the spirit or scope of the system and/or the claims of the embodiments illustrated. As referred to herein the term support generally refers to orthotics and orthopedic casts, braces, and splints, specifically, for the support and immobilization of a joint and limb.

Figure 1A:
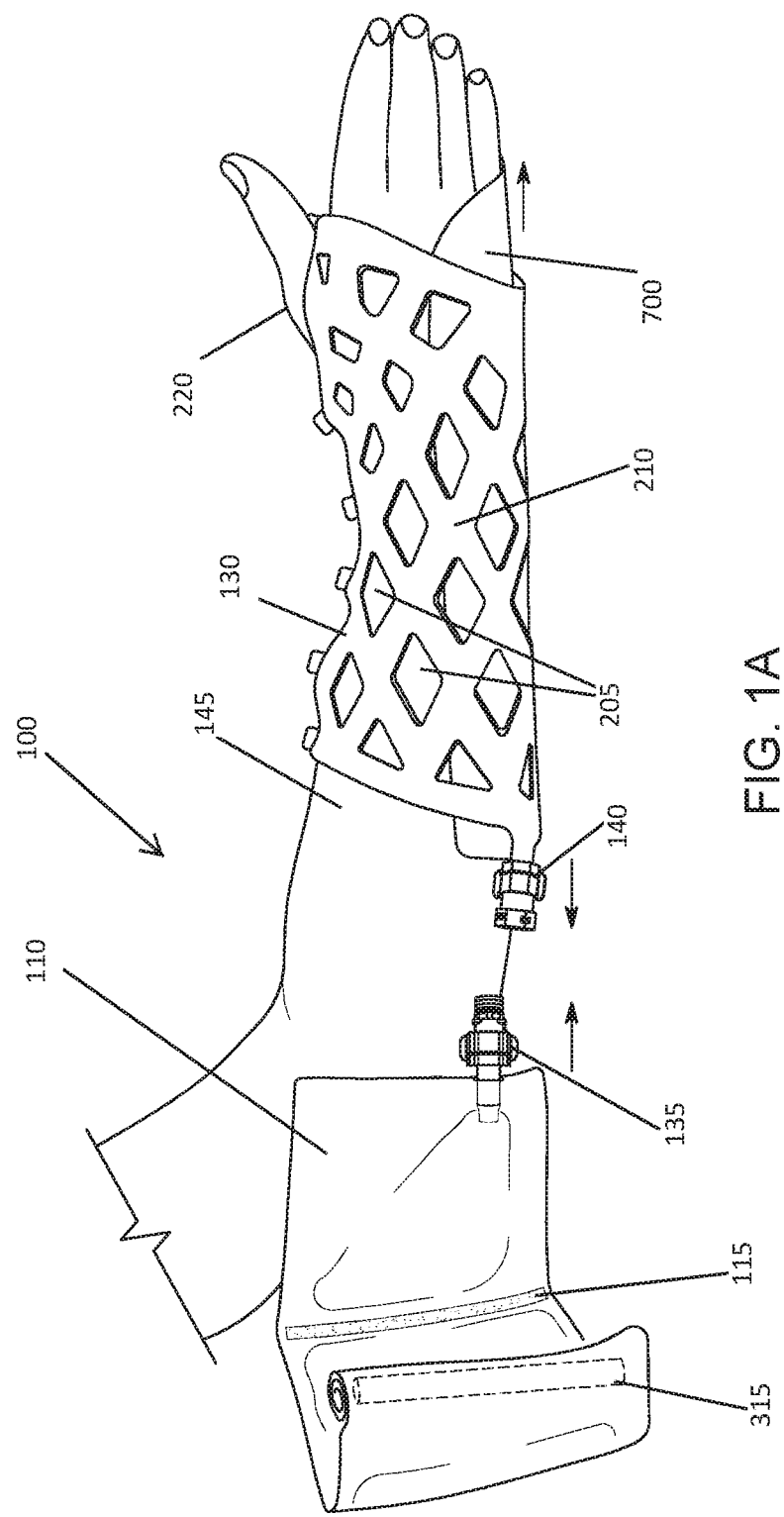
FIG. 1a shows a perspective view of system embodiment comprising an external pack to be connected to a flexible sleeve over an affected body area to construct a support.
Figure 1B:
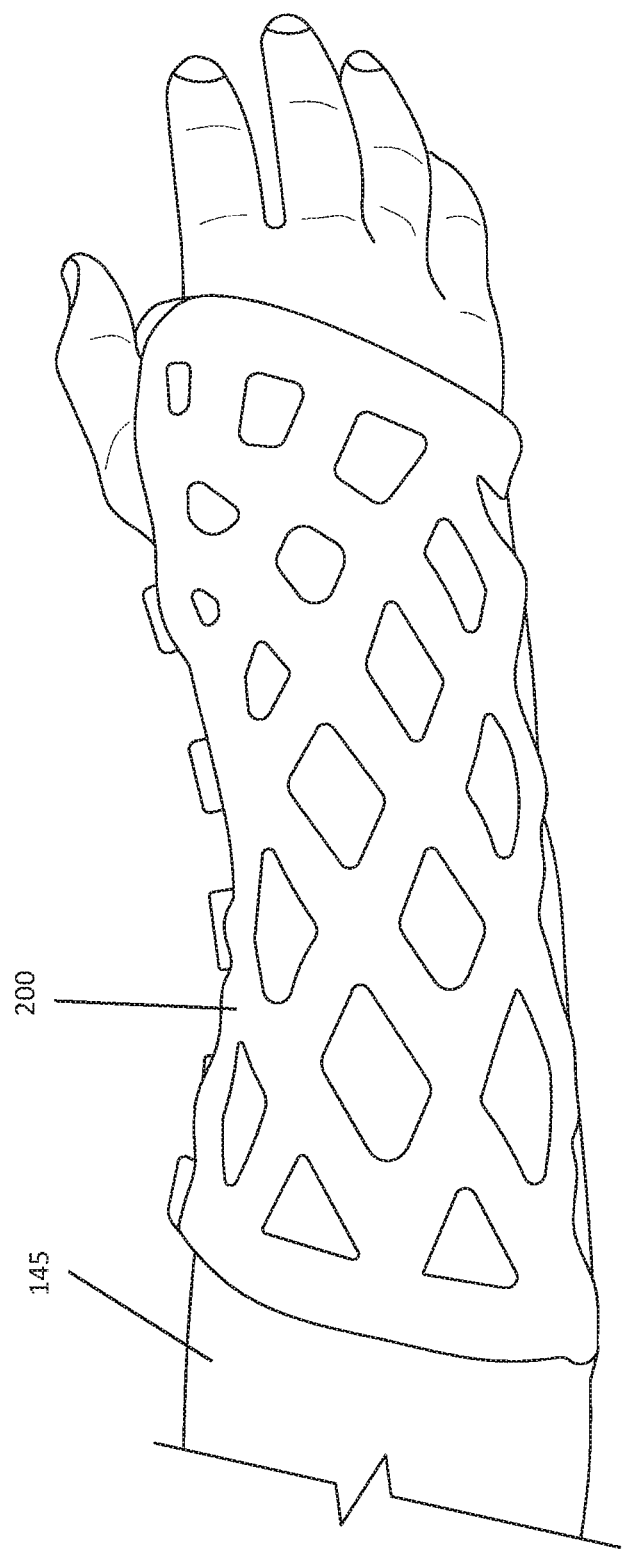

Referring now to FIG. 1a, illustrated is a preferred embodiment of the overall system 100 invention comprising of an external pack 110 with frangible seals 115/120 and filled with at least one liquid. The external pack 110 is connected to the flexible sleeve 130 via a series of valves 135/140 and is used to inject the liquid(s) into the flexible sleeve 130. The filled sleeve can then be molded and allowed to solidify over an affected body area 145. When constructed in accordance with one or more embodiments of the system 100 invention, a support 200 is formed (FIG. 1b). FIGS. 1a and 1b show the preferred embodiments of system invention in the form of a short arm support 200 that is applied to the distal forearm and wrist 145.

Figure 2B:
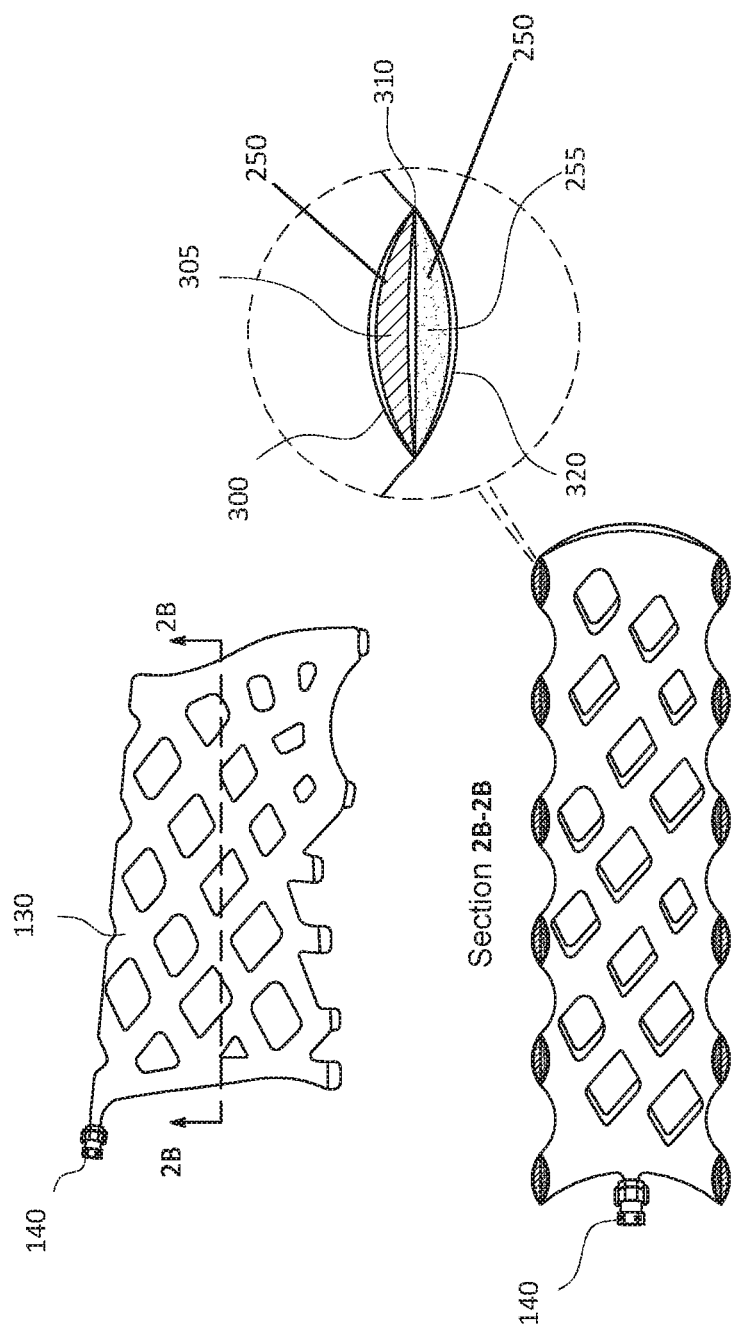
FIG. 2b is a cut-away view of the completed embodiment in FIG. 2a, sectioned along the plane showing the layers of the of the support.

FIG. 2a shows the initially flexible sleeve 130 of the system consisting of a network of elastic tubing that is interlaced at a plurality of junctions 210 to form a unique lattice 205 structure. The lattice 205 is configured to have multiple lumen 250, shown in FIG. 2b, in which varying thicknesses of the elastic tubing layers 300/310/320 are stacked. This arrangement of material better accommodates internal pressures from filling, reduces kinking in the material, and maintains elasticity in the sleeve 130. The sleeve 130 is preferably made from a medical grade polyurethane blend that is nonporous and biocompatible, that can make the flexible sleeve 130 waterproof and resistant to bacterial accumulation or tissue ingrowth of the skin underneath. The material itself is also resistant to UV degradation with a relatively high tear resistance to make it suitable for outdoor use. In an ideal variation, the sleeve 130 is created by extruding the polyurethane blend into thin sheets of film that are then cut and sealed using various techniques not limited to welding, heat, or adhesives.

Apertures 220 are included in the lattice 205 structure to allow for expansion of the tubing while it is being applied to a subject, and also allow for the flow of air and water to the subject's skin. Various sized apertures 220 may be included to accommodate body features such as a thumb, fingers, or wrist. The lattices 205 of the sleeve 130 are shaped and patterned such that the structure mimics the appearance and functionality of naturally occurring formations known to promote shape adaptability and load bearing in both transverse directions. The windowed design also permits air or water to reach the skin underneath the support and encourage rapid filling of the liquid(s) throughout the internal sleeve 130 structure. The overall profile of the sleeve 130 was constructed following recommendations of ergonomic clothing design, which in the instance of the short arm support 200 shown in FIG. 1a, is a custom glove profile. Dimensioning the design accurately to specific body areas is driven by NASA listed anthropometric data. Also, the final configuration for the network of tubing varies according to the specific body area 145 affected, as well as the differing support requirements for treatment across injuries. Lastly, the breathability of the latticed 205 sleeve design allows the underlying skin to be routinely washed, dried, and easily checked by physicians; options that are otherwise unavailable with standard casting methods.

Figure 12:
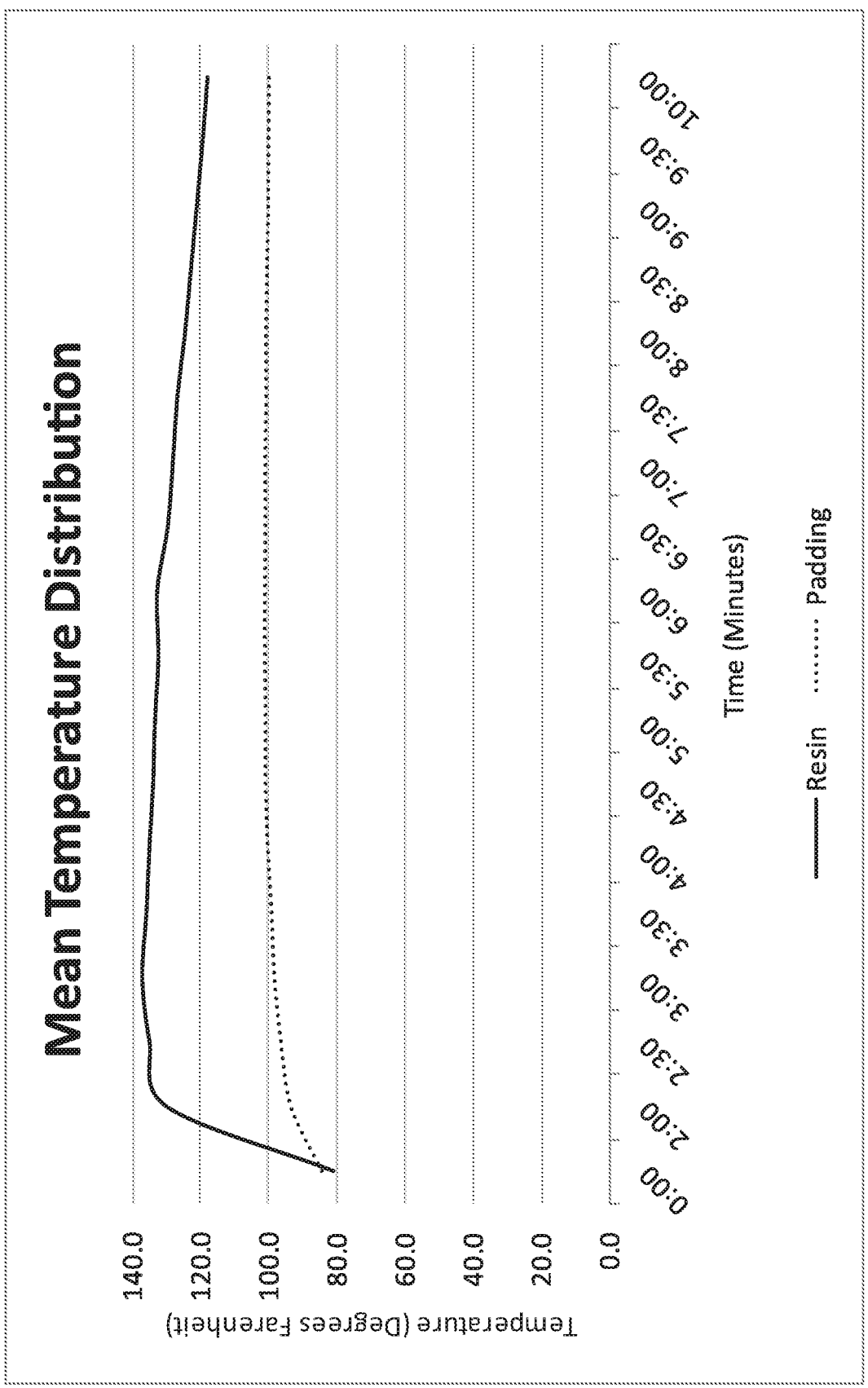
FIG. 12 is a diagram illustrating the thermal resistance of one embodiment of the padding layer.

A flowable gel-like material that can be injected into the lumen of the lattice structure that directly abuts the skin offers cushioning 255 to the invention. This padding 255, shown in FIG. 2b, must span the entire surface area of the flexible sleeve 130 to not only provide a soft material between the body and rigid structure of the support 200, but also act as a protective thermal-resistant layer against the heat generated during the hardening of resinous liquid(s). Many resinous liquid mixtures can reach temperatures over 150° F. when hardening to their solid form, which when exposed to unprotected skin, can cause severe burns and pain. The thermal-resistance of the padding was selected specifically to prevent transfer of the exotherm to the skin and maintain exposure to less than 113° F., as defined by NASA safety standards. FIG. 12 illustrates the thermal resistance of this preferred embodiment using the flowable padding layer 255 compared against skin surface temperatures recorded without use of a padding layer. FIG. 2b shows a cutaway view of the embodiment from FIG. 2a, sectioned to expose the layers of the of the support 200. An enlarged cross-sectional view of the lattice structure includes a thick flexible sleeve layer 300, resin 305, thin flexible sleeve layer 310, internally encased flowable thermo-resistant padding 255, and a final thin flexible sleeve layer 320. It should be noted, the breathability of the latticed sleeve 130 is not impeded by the padding 255 layer since it is internally encased within the multi-lumen structure. Additionally, the minimal thickness of the padding reduces the bulkiness and weight of the support 200, while still promoting anatomical conformity of the support and overall patient comfort. A valve 140 is secured to at least one inlet of the flexible sleeve 130 that is used to connect to the valve 135 component of the external pack 110 and allow the transfer of liquid(s).

Figure 3A:
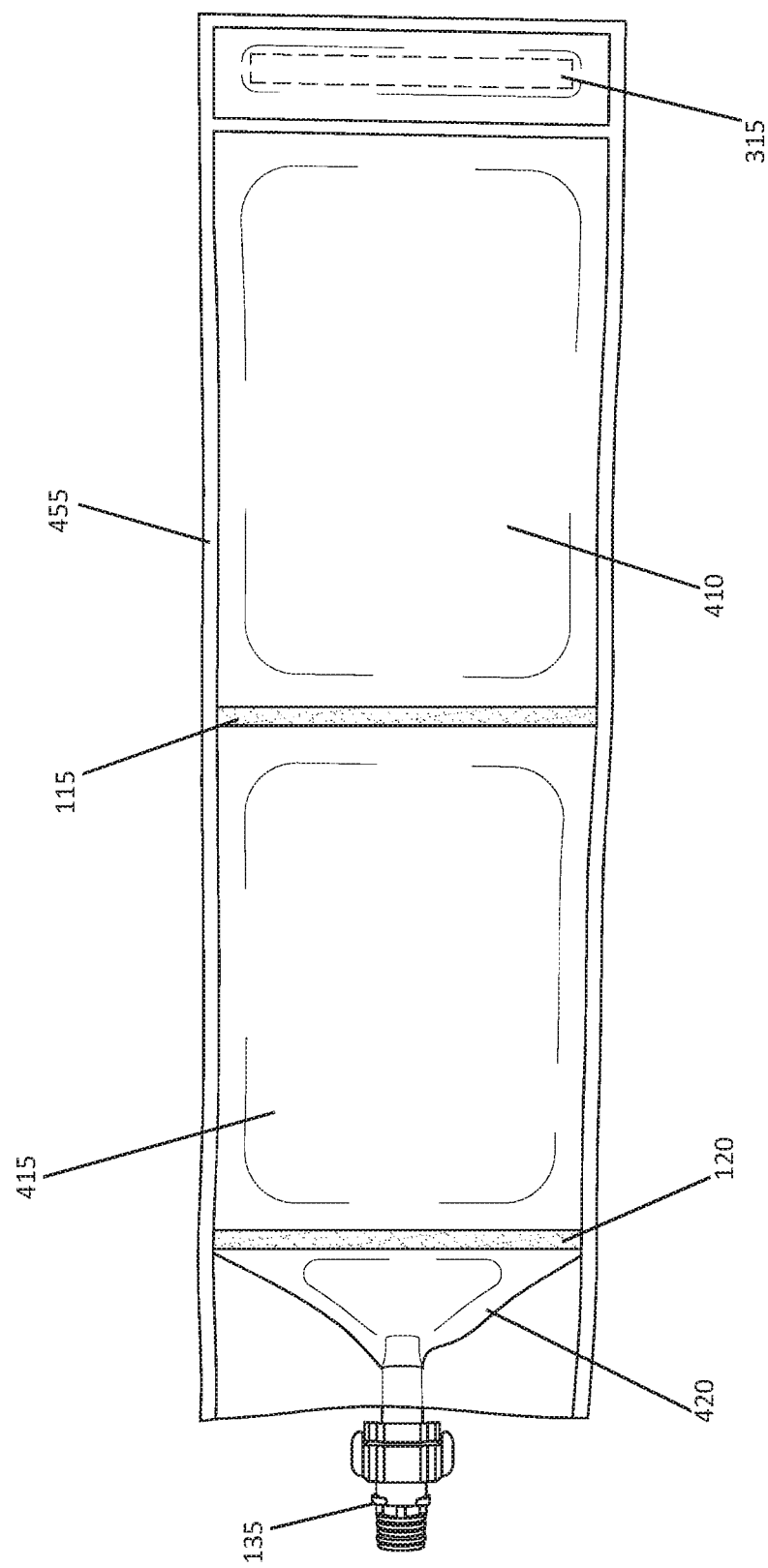
FIG. 3a is an illustration of the preferred embodiment for the external pack.

FIG. 3a is an illustration of the preferred embodiment for the external pack 110, comprising of a handle 315 that is secured internally, a valve component 135, and at least two frangible seals 115 and 120 to create at least three chambers 410, 415, 420 used to contain liquids including a resin, a catalyst, or other additives separately. All chambers 410, 415, 420 may be filled with liquids, whereas the smaller additive chamber 420 may alternatively remain void of liquid to act as an antechamber and protect against degradation of the valve component 135 or oxidation of the other contained liquids.

In the preferred embodiment, the chambers 410, 415, 420 are defined to hold a polyurethane resin, a catalyst, and a coloring agent, that when mixed together and injected into the flexible sleeve 130, transform into a rigid structure of a particular color in the form of the sleeve 130 lattice. As such, it is preferred that the flexible sleeve 130 is transparent or translucent to allow viewing of the colored resinous liquid flowing throughout and showing any air bubbles that need to be guided manually out through the valves 135/140. The transparency of the flexible sleeve 130 material also gives the user the opportunity to view the curing process of the resin 425/305 and determine when gelling has occurred. At which point, the product may be manually molded to better conform about the limb until it transforms into a completely hardened support 200. The final hardened resin 305 is of a single homogenous color with a minimum Shore Hardness of at least 70D. Alternative embodiments include chemical additives such as retardants or accelerants contained in the small additive chamber 420 of the external pack 110 that alter the curing time of the hardenable liquid in order to vary the use of the system making it suitable for many applications.

In an alternative application, the hardenable liquids, defined to include a polyurethane resin and catalyst, are mixed thoroughly prior to the bursting of the final frangible seal 115/120 separating the colorant. The resinous contents are not mixed further after the coloring agent has been introduced, but rather immediately injected into the network of tubing. This alternative application method creates a different coloring scheme in which a tie-dye effect is seen throughout the entire lattice structure, rather than a single homogenous color.

Figure 3B:
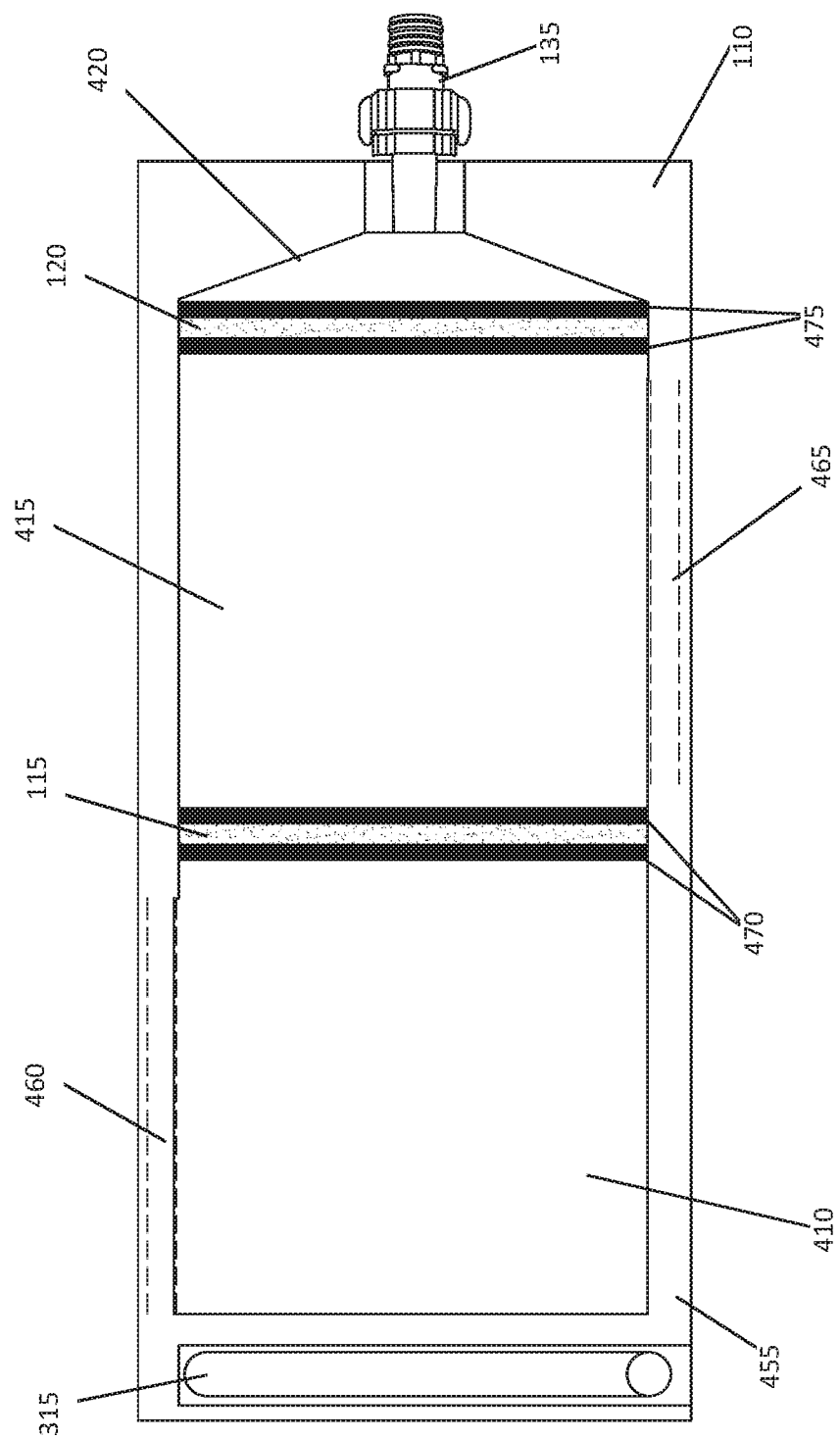
FIG. 3b is a top view of the external pack from FIG. 3a further illustrating an internal layer and division of sections thereof.

FIG. 3b is a top view of the embodiment from FIG. 3a with the topmost layer of material removed to expose the internal structure of the external pack 110. The perimeter seams 455 of the external pack 110 are permanent, non-frangible seals created by stacking two materials atop of one another and bonding them together. Two openings 460/465 in the perimeter seam 455 are used for meter-filling of the liquid contents into the chambers 410/415 of the external pack 110 prior to sealing the external pack layers. These fill openings 460/465 are then closed permanently post-filling using methods such as impulse sealing. For the portion of the pack that is a temporary frangible seal 115/120, a third material is introduced between the existing two external pack layers then lightly bonded together (FIG. 3b). The seal of all three materials is weaker than the perimeter seam 455, such that when external pressure is applied to the frangible seal 115/120, only the frangible seal 115/120 will burst and allow the separated liquids to mix. This portion of the external pack is known as the burst zone 470/475. A valve 135 secured to an opposing end of the external pack 110 is used to connect this component to the valve 140 on the flexible sleeve 130 and allow the transfer of liquid(s) between the two.

Figure 6:
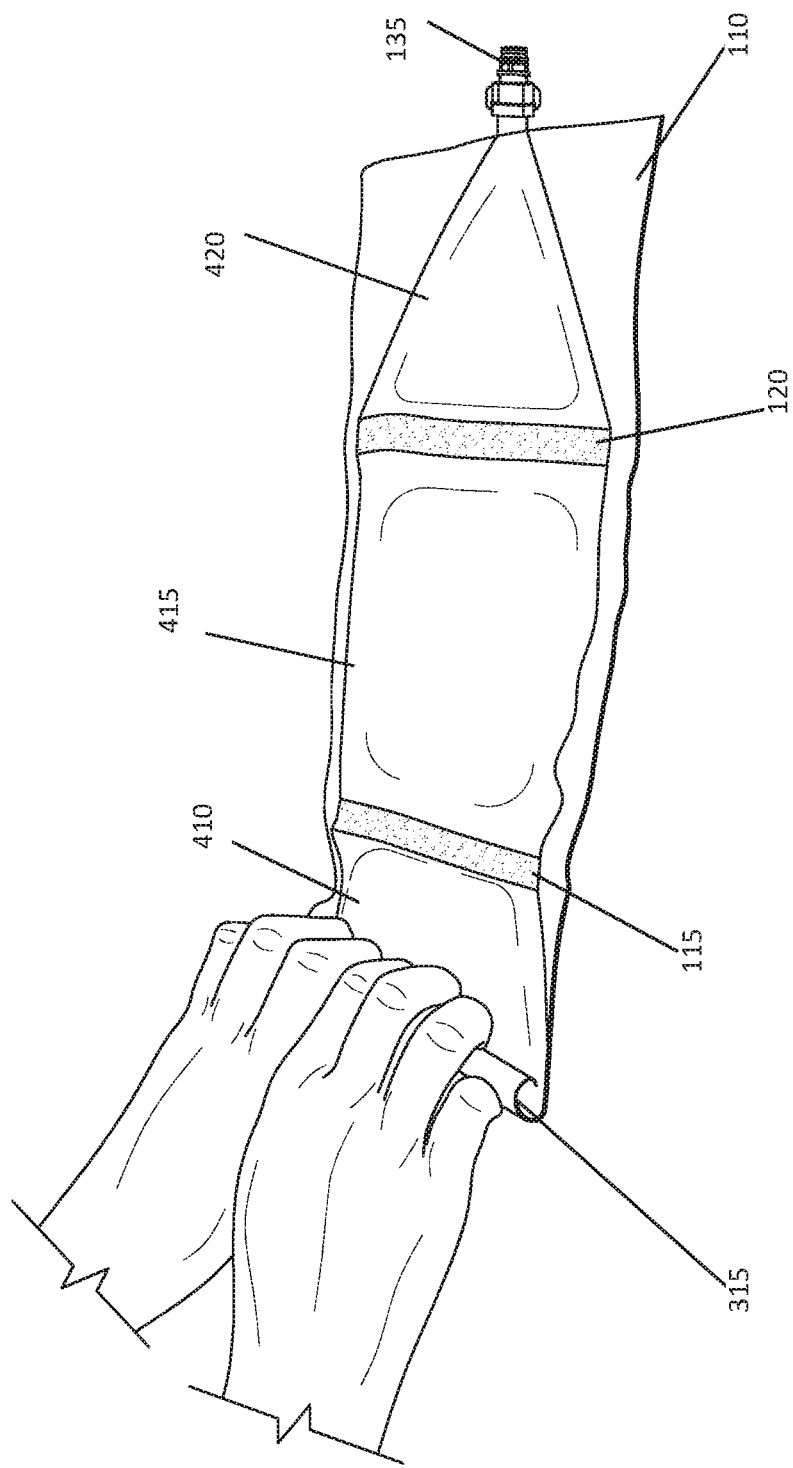
FIG. 6 is an illustration of a method of use of one embodiment for the external pack.

Referring to FIG. 6, a perspective view of one embodiment of the external pack 110 illustrates the use of the internal handle 315 to roll and apply the pressure needed to burst the frangible seals 115 and 120, and thus initiating the mixing of liquids in adjacent chambers 410, 415, 420 initially separated.

Figure 7A:
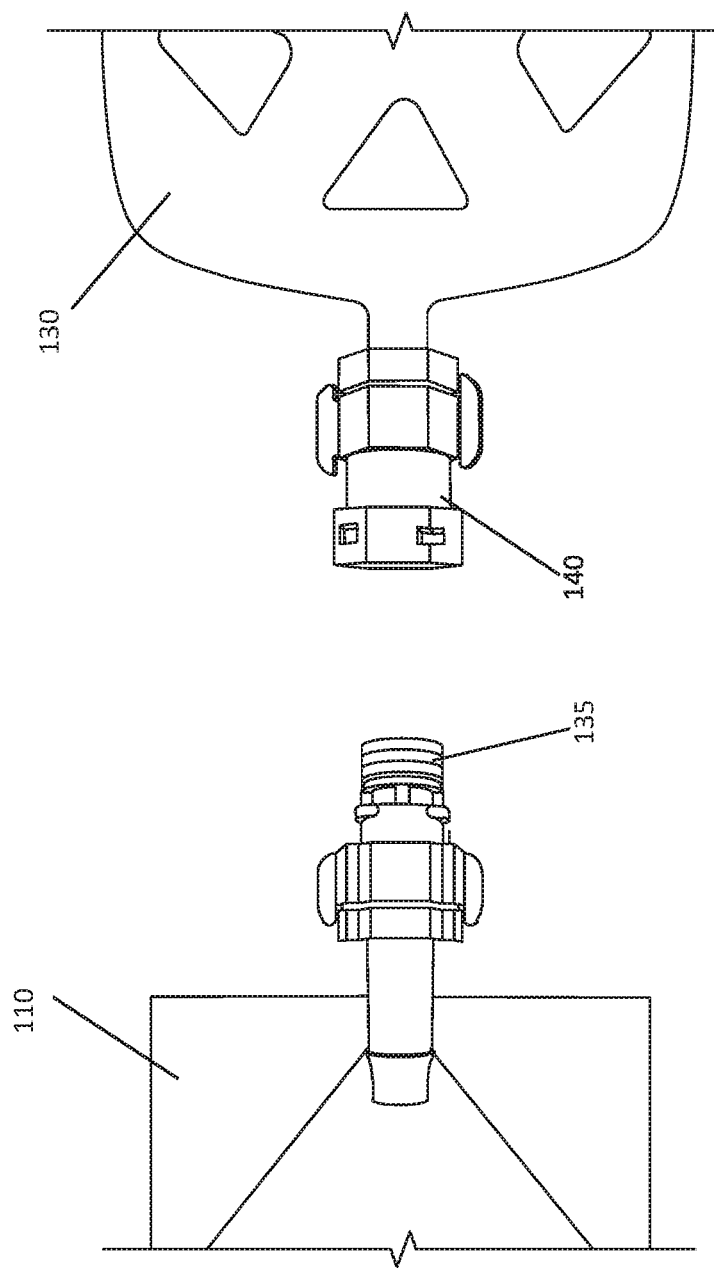
FIG. 7a is an enlarged view of the connecting components used to engage embodiments shown in FIG. 1a of the system invention.
Figure 7B:
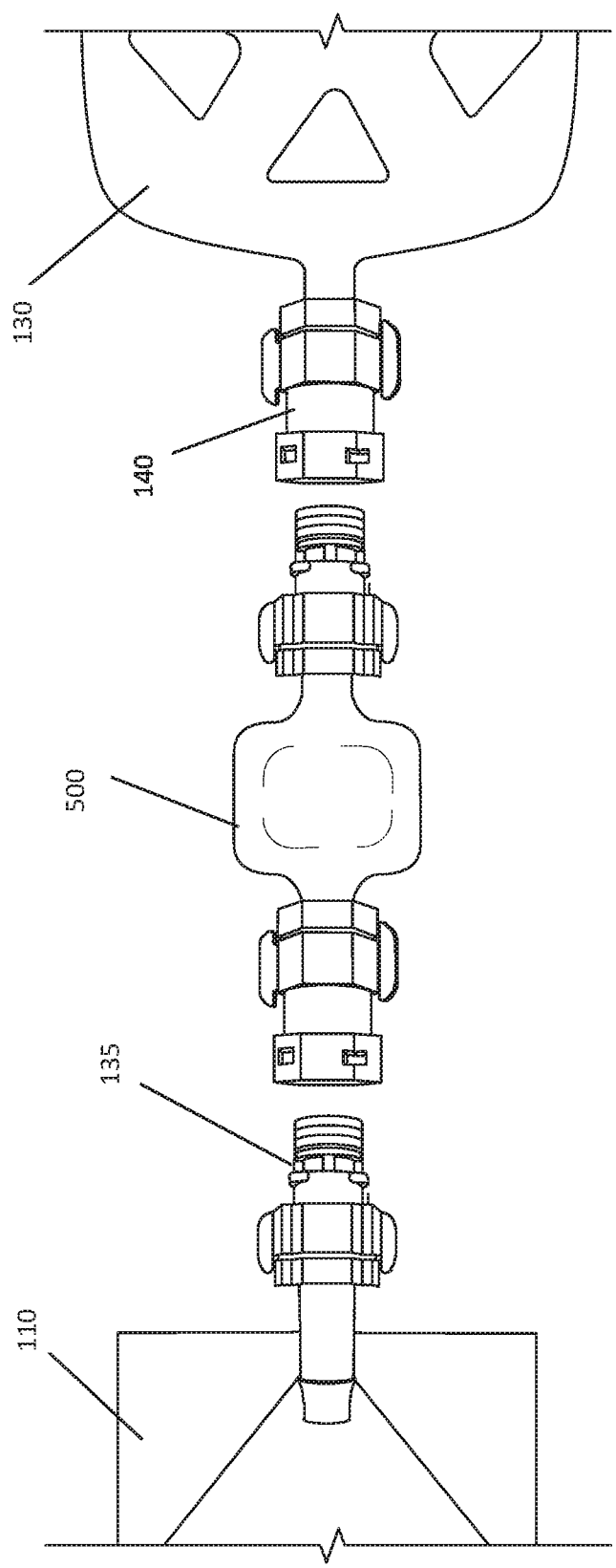

FIG. 7a is an enlarged view of the valve system 135/140 used to connect and secure the external pack 110 to the flexible sleeve 130. The quick coupling valves 135/140 engage and lock the system components easily to begin the transfer of the liquid(s) into the flexible sleeve 130. The diameter of the valve spout was selected to encourage rapid dispensing of the resinous material without straining the user to apply enough pressure. In the preferred application, virtually all liquid contents in the external pack 110 are transferred to the flexible lattice structure. The two-way flow of the valves 135/140 also permits removal of excess air within the network of tubing that could potentially compromise the structural integrity of the final rigid support 200. After liquid transfer has been completed, a built-in shut-off feature of the valves 135/140 prevents any spilling of liquids during disconnection and the external pack 110 can then be disposed. FIG. 7b illustrates an optional component of the system to introduce coloring agents in the liquid mixture. A cartridge 500 contains any dye or additives such as glitter to enhance to appearance of the support 200 and provide an alternative means of introducing dye 440 to the system.

Figure 4:
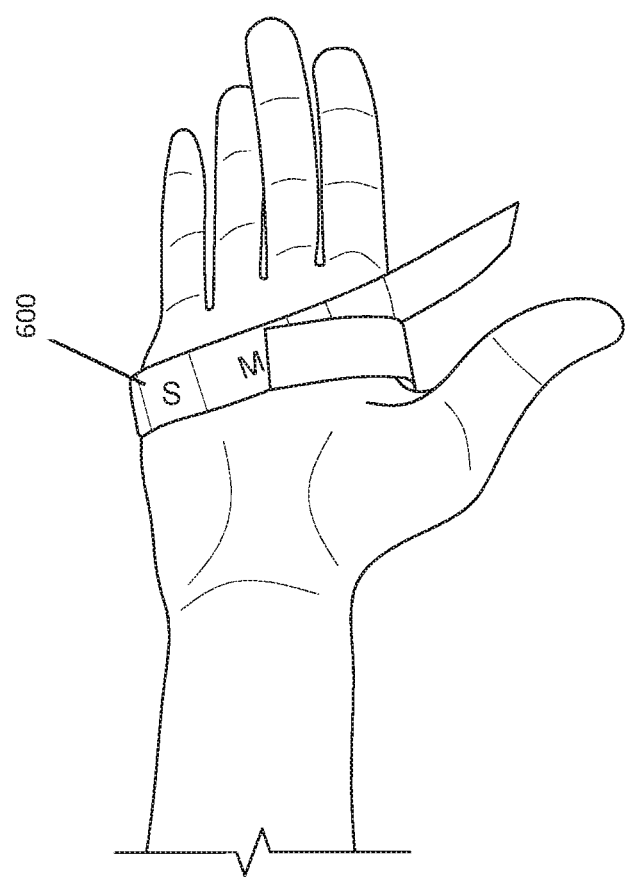
FIG. 4 is an enlarged view of an optional component used in one or more of the system embodiments.
Figure 5A:
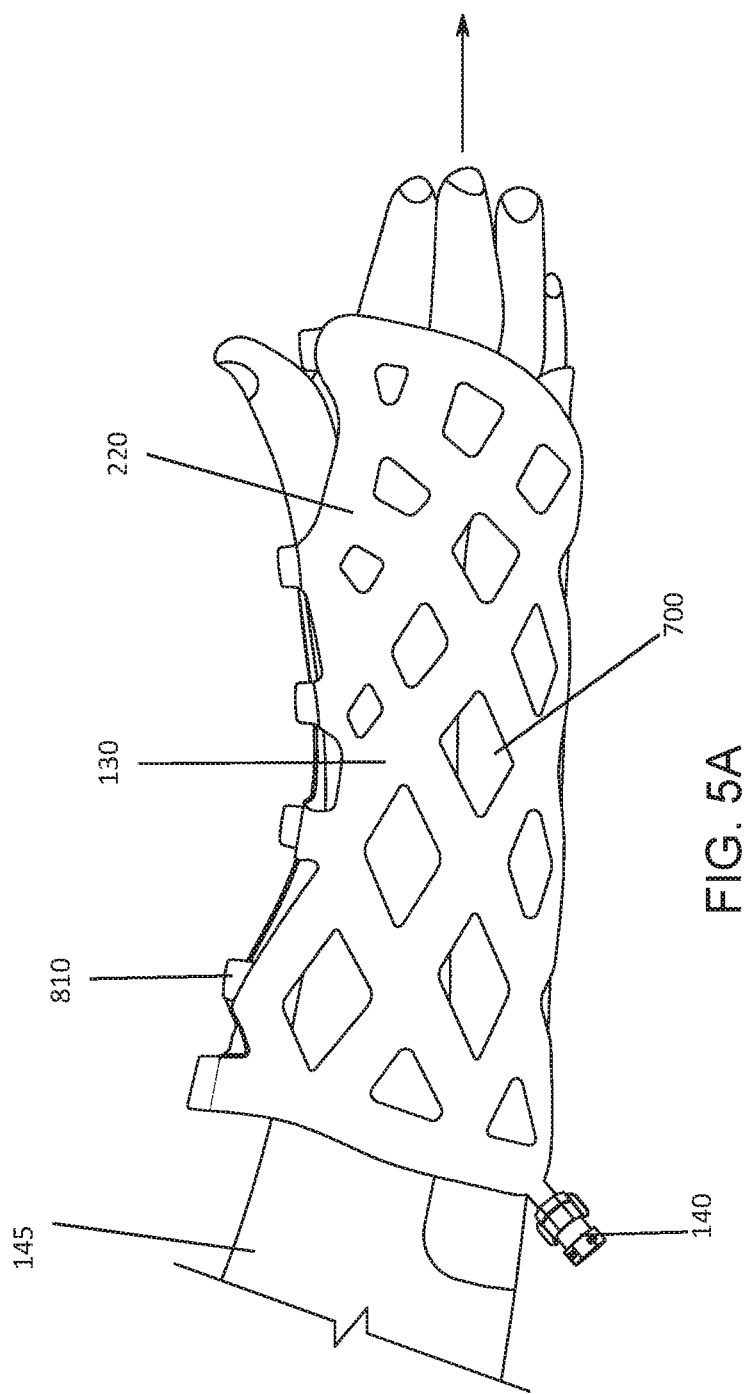
FIG. 5a is an illustration of one aspect of the system application over the affected body area. In the preferred embodiment, an optional component is used to assist with the application.
Figure 5B:
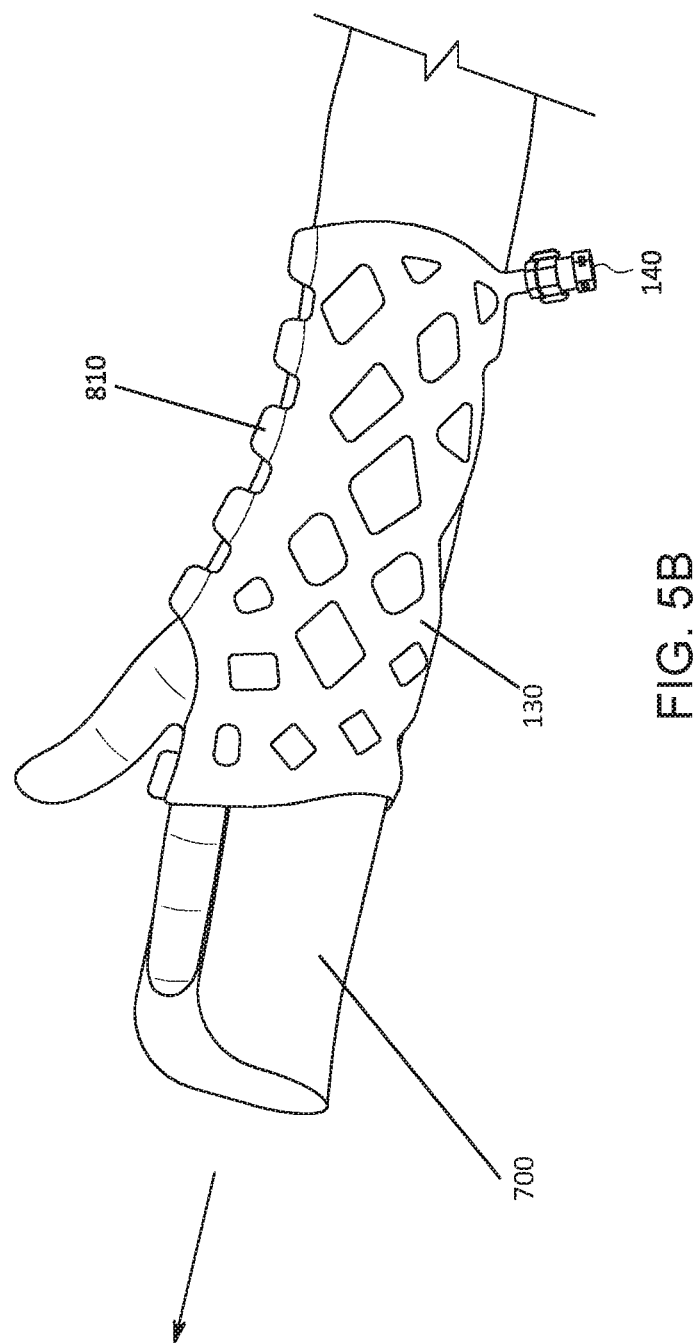
FIG. 5b is a perspective view of the removal of the optional component in FIG. 5a after it has been used.

Prior to bursting the frangible seal 115 of the external pack 110 and initiate curing of the resinous liquid mixture, the flexible sleeve 130 must first be fitted and placed over the affected area. To properly fit the sleeve 130, a measuring tool 600 is used in one or more of the system embodiments. FIG. 4 demonstrates the method of use for a short arm support to check palm circumference of the hand 145 and determine the correct size of support 200 for application. FIG. 5a is a perspective view of one aspect of the system application in which the flexible sleeve 130 is slid over the affected limb. In one embodiment, a removable plastic insert 700 within the flexible sleeve 130 is used to assist with sliding. The optional plastic insert 700 is then removed, and the sequence of bursting frangible seals 115 and 120 of the external pack 119 can begin (FIG. 5b and FIG. 6).

After all frangible seals 115/120 of the external pack 110 have been burst and contents mixed sufficiently, the valve components 135/140 of the external pack 110 and flexible sleeve 130 can then be connected to fully transfer liquid into the sleeve 130 (FIG. 1a and FIG. 7a). Any air bubbles present in the sleeve 130 may be manually guided out through the two-way valve 135/140. The valves are then disconnected, and the now empty external pack 110 is discarded. This complete process takes ideally no more than 3 minutes, at which point the resinous liquid has begun to gel and is no longer flowable but still very malleable.

Figure 9:
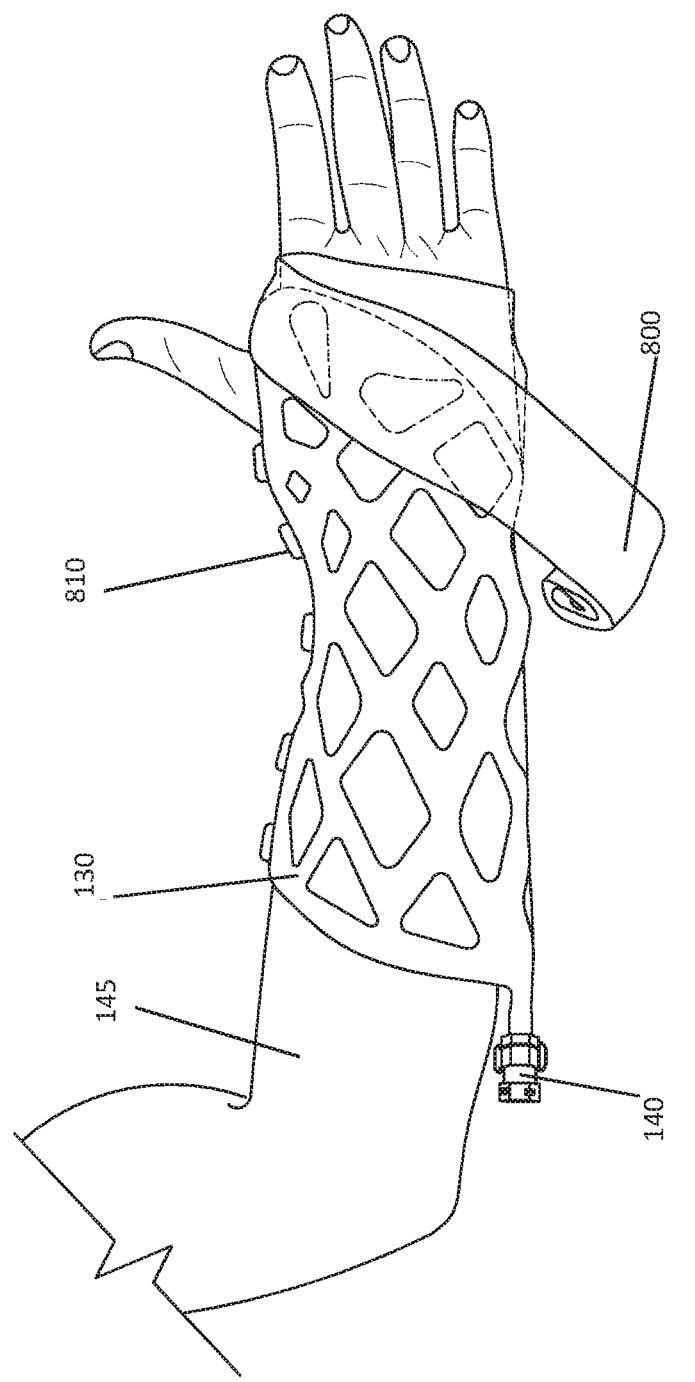
FIG. 9 is a perspective view of an optional component used in one or more of the system embodiments to wrap around the affected body area and support.

There is a period in which the filled sleeve 130 can be manually molded about the limb prior to the resin 425 fully curing into its rigid structure. An optional elastic wrap 800, shown in FIG. 9, made of a thin and breathable material can be used to wrap around the limb under the flexible sleeve 130 to better conform the support 200. The elastic wrap 800 allows for heat created from the curing of resin to dissipate. Sufficient curing of the support 200 can occur within 10-15 minutes of initiating the application process, at which point the elastic wrap 800 is removed and valve component 140 of the support is cut off with shears 805 (FIG. 8). Both elastic wrap 800 and valve 140 can be disposed. The final rigid support 200 is shown in FIG. 1*b*.

Figure 10:
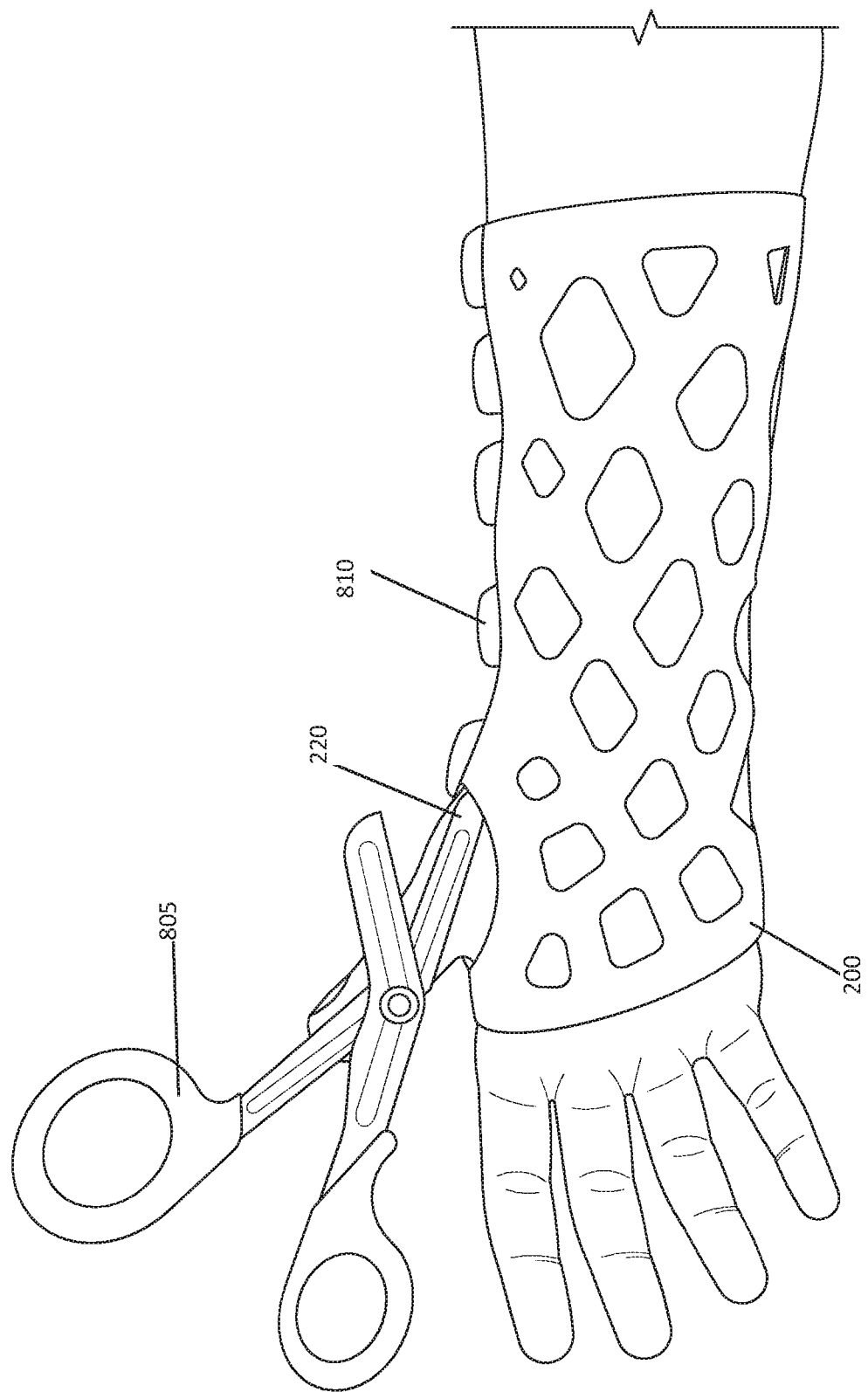
FIG. 10 is a perspective view of the preferred method of removal used in one or more embodiments of the system.
Figure 11A:
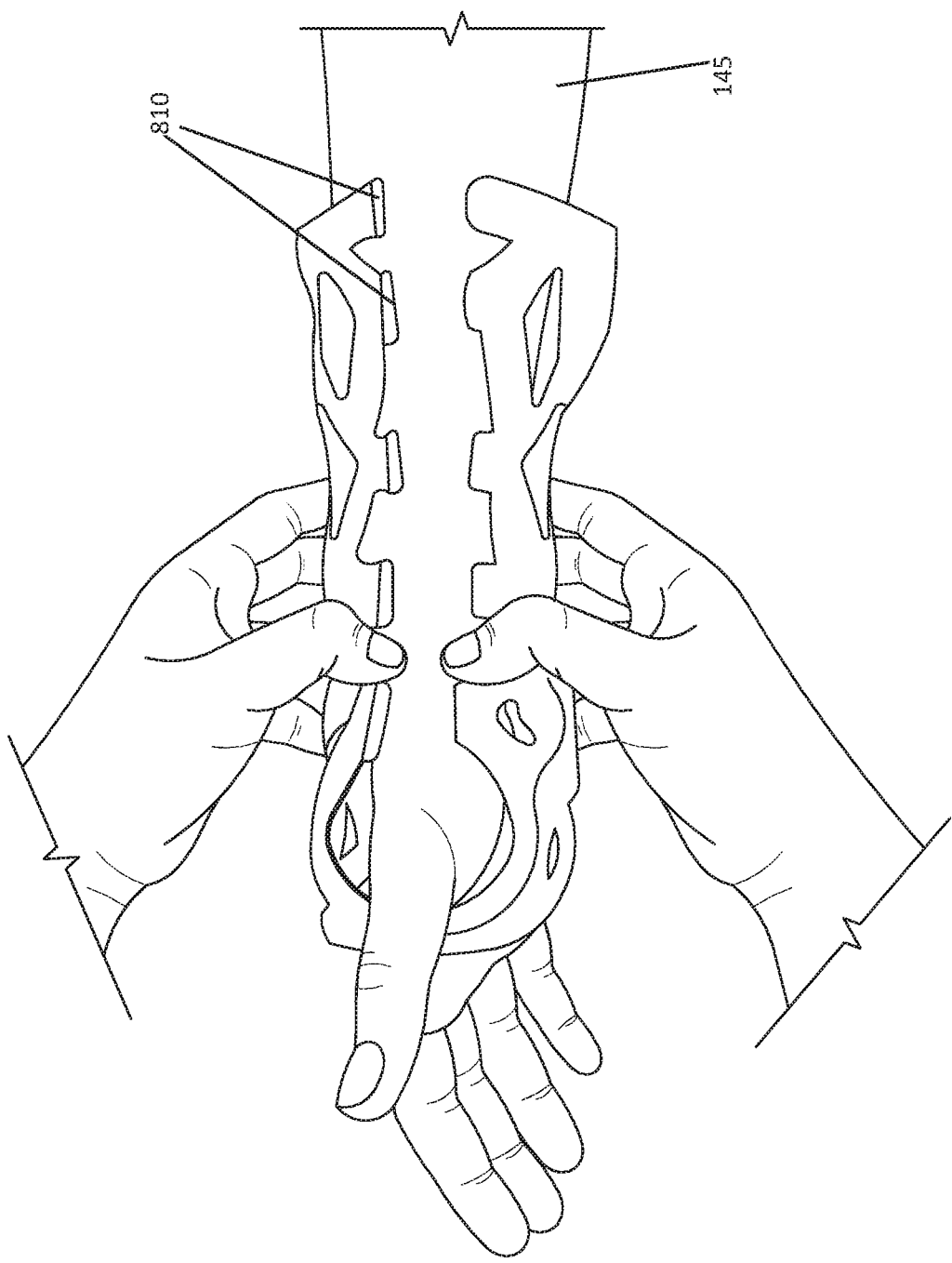
FIG. 11a is a top view of the preferred method of removal of the embodiment.
Figure 11B:
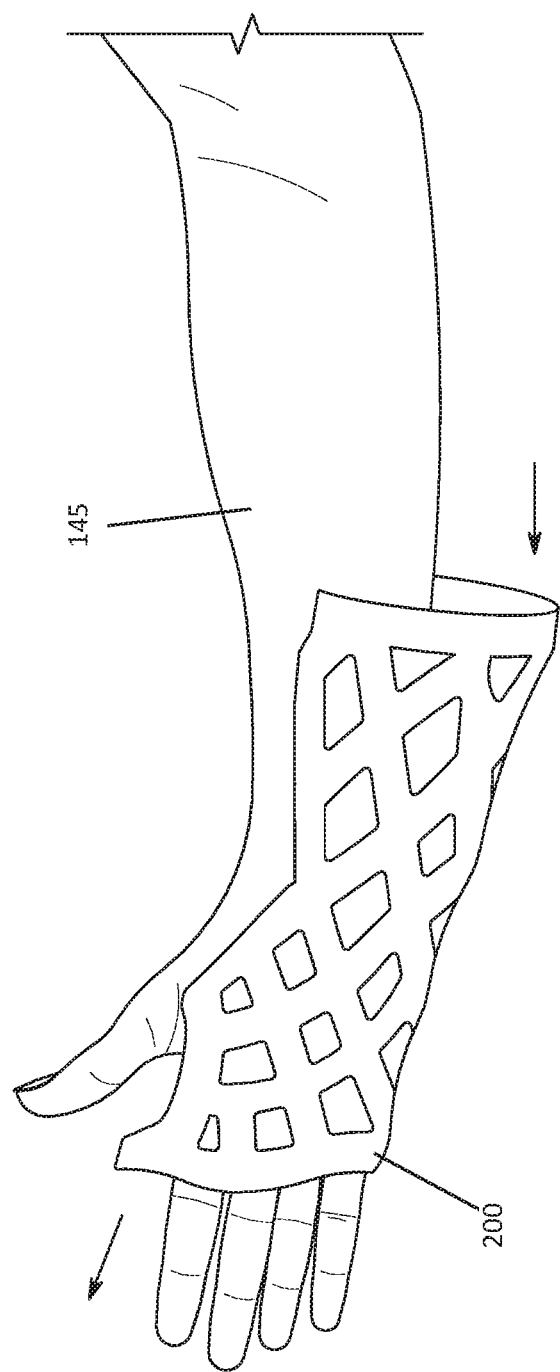
FIG. 11b is a perspective view of one aspect of removal of the embodiment.

In a preferred method of removing the support, clinical shears 805 are used to cut through the tabs 810 along the cutting seam avoiding all resinous material (FIG. 10). The tabs 810 are extensions of the flexible sleeve 130 material, that are the result of sealing the flexible sleeve 130 structure closed during its fabrication and creating a seam for cutting. No resinous or padding material is found in the tabs 810 of the support 200. The support 200 can then be manually spread open and removed from the affected body area 145, as demonstrated in FIGS. 11*a* and 11*b*. The support 200 can then be disposed of normally. This preferred process of removal eliminates the messy and bothersome production of dust particles caused by using cast saws. The method also reduces the trauma of noisy and potentially harmful sawing can have on young patients. This improved process of removing the support 200 also reduces the cost of supplies and reduces the time required from physicians to spend with each individual patient.

Figure 13A:
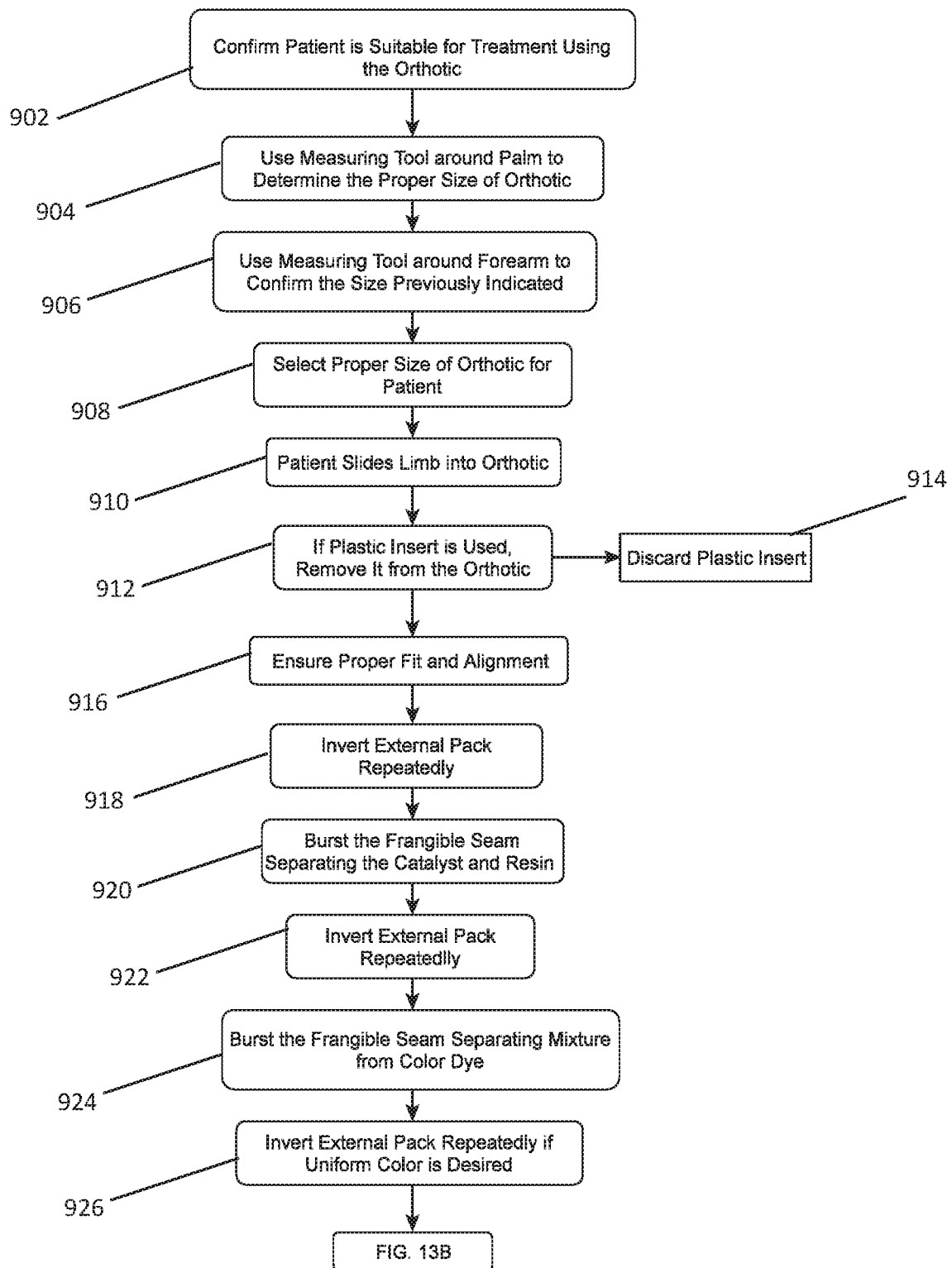
FIGS. 13a & 13b illustrate a flow diagram of one embodiment of the system invention illustrating the preferred method of application, creation, and removal.
Figure 13B:
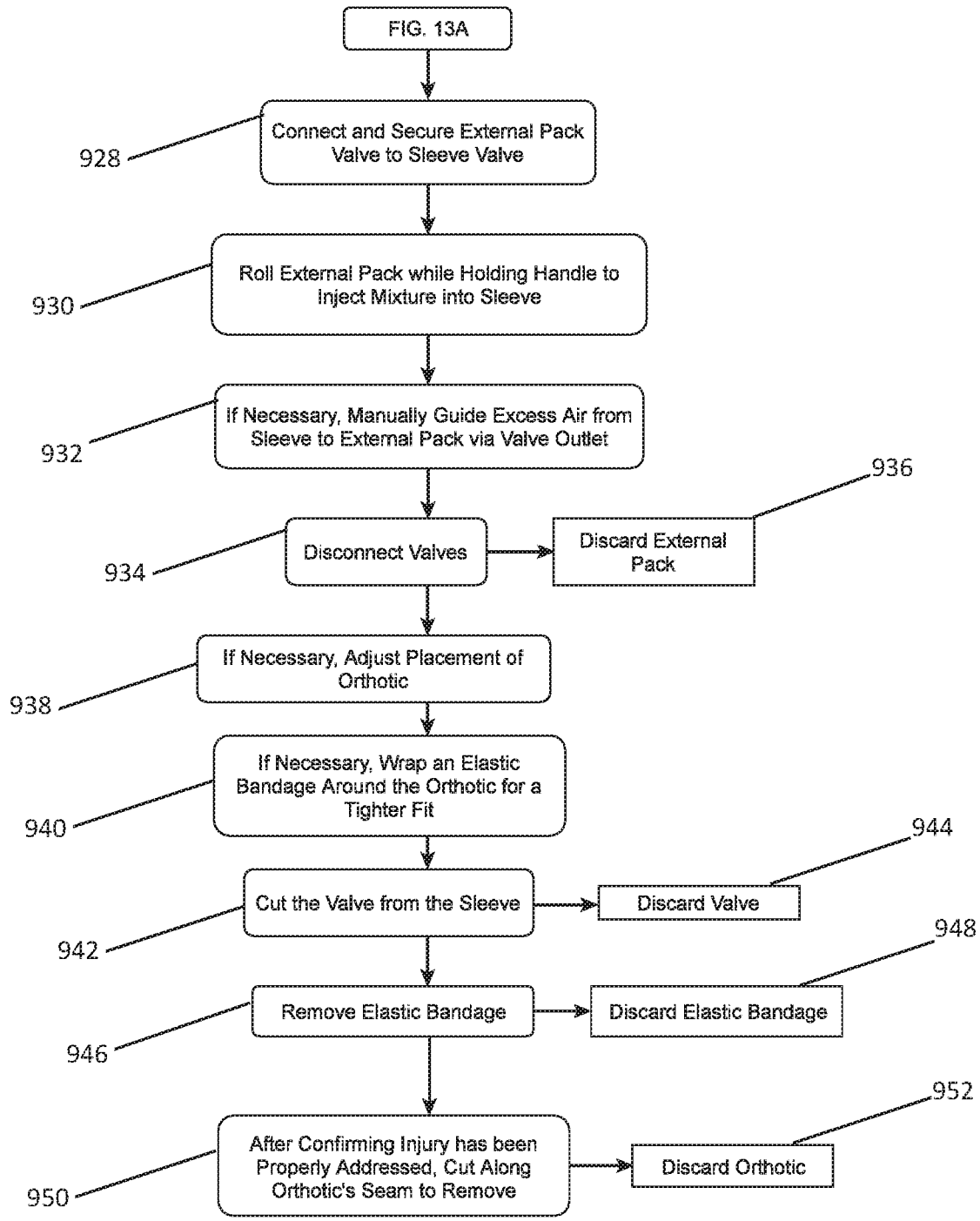

A flow diagram, FIGS. 13*a* and 13*b*, of the preferred embodiment of the system invention 100, illustrates this method of application and removal of the support 200 detailed above. As outlined, BOX 902, a patient is confirmed suitable for treatment using the support embodied herein. A measuring tool around the patient's palm is used to determine the proper size of the support, BOX 904. The measuring tool may be further used around the forearm to confirm the size, BOX 906. Based on the measurements, the proper sized support for the patient is selected, BOX 908. The patient then slides the limb into the support, BOX 910. If a plastic insert is used, it can be removed from the support, BOX 912, and then discarded, BOX 914. A proper fit and alignment should be considered at this particular time, BOX 916. The external pack should be inverted, BOX 918 and the first frangible seam can be burst allowing the catalyst and the resin to mix, BOX 920. The external pack should again be inverted, BOX 922. The second frangible seam can be burst to mix in the colorant or additive, BOX 924. The external pack should again be inverted if a uniform color is desired, BOX 926. The external pack should be connected to the sleeve, BOX 928, and the external pack rolled while holding the external pack handle to inject mixture into the sleeve, BOX 930. If necessary, excess air from the sleeve can be manually guided out of the sleeve to the external pack via the valves, BOX 932. The valves can be disconnected, BOX 934 and the external pack discarded, BOX 936. If necessary, the placement of the support can be adjusted, BOX 938. A wrap or elastic bandage may be placed around the support for a tighter fit, BOX 940. The valve from the sleeve can be cut once the filled sleeve hardens, BOX 942 and then discarded, BOX 944. The elastic bandage can also be removed, BOX 946, and discarded, BOX 948. Once the injured area has been addressed and the support is ready to be removed, the support can be cut along the seam (or tabs) to remove it from the patient, BOX 950 and then discarded, BOX 952.

From the foregoing and as mentioned above, it will be observed that numerous variations and modifications may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

We claim:

1. A system to provide a support to a body area, the system comprising:
 a flexible sleeve comprising:
  a network of flexible non-porous tubing interlaced at a plurality of junctions to form a lattice structure that defines a plurality of apertures configured to allow for a flow of air and water to the body area and to accommodate for unique contours of the body area, wherein the lattice structure comprises:
   a bottom layer of the network of flexible non-porous tubing configured to contact the body area when in use;
   a top layer of the network of flexible non-porous tubing;
   a middle layer of the network of flexible non-porous tubing positioned between the bottom layer and the top layer and connected to the bottom layer and the top layer to form (i) a first lumen defined by the bottom layer and the middle layer, and (ii) a second lumen defined by the top layer and the middle layer;
   a thermo-resistant padding positioned in the first lumen, wherein the thermo-resistant padding comprises a flowable and injectable material that cures within the first lumen into a non-flowable solid material; and
   a longitudinal seam in the network of flexible non-porous tubing extending from a first end of the lattice structure to a second end of the lattice structure, wherein the longitudinal seam includes the bottom layer, the middle layer, and the top layer, and wherein the longitudinal seam does not include the first lumen or the second lumen such that the longitudinal seam is void of both the thermo-resistant padding and a resinous material; and
 an inlet in fluid communication with the second lumen of the lattice structure to permit the flow of fluids into and out of the network of flexible non-porous tubing; and
 an external liquid pack comprising:
  a first chamber and a second chamber separable from each other by a first frangible seal, wherein the first chamber includes a catalyst, wherein the second chamber includes a liquid resin, and wherein, when the first frangible seal is broken, the catalyst and liquid resin mix;
  a third chamber separable from the first and second chambers by a second frangible seal;
  an outlet in fluid communication with the third chamber, wherein the outlet is configured to mate with the inlet of the flexible sleeve, and wherein, when the outlet is secured to the inlet and the first frangible seal and the second frangible seal are broken, the mixed liquid resin and catalyst flow into the second lumen of the lattice structure and transforms into a solid such that the flexible sleeve hardens into the support for application to a body area; and
a rigid handle secured on an end of the external liquid pack opposing to the outlet; and
a cartridge holding a predetermined color additive defined as being a non-white color additive, the cartridge includes an inlet and outlet to mate with the outlet on the external liquid pack and the inlet on the lattice structure, and wherein the lattice structure is substantially transparent, such that during mixing and transformation, liquid resin and catalyst flow through the cartridge and mix with the color additive to create a non-white colored support.

2. The system of claim 1, wherein a thickness of the top layer is greater than a thickness of the middle layer and a thickness of the bottom layer.

3. The system of claim 1, wherein the third chamber is empty to buffer the liquid resin and the catalyst from the outlet to protect against degradation of the outlet or oxidation of the liquid resin and/or the catalyst.

4. The system of claim 1, further comprising a color additive contained in the third chamber, wherein the color additive is a non-white color, wherein the lattice structure is substantially transparent, and wherein the color additive when mixed with the liquid resin and the catalyst in the lattice structure is configured to provide a predetermined non-white color to the support.

5. The system of claim 1, further comprising an additive contained in the third chamber to adjust one or more properties of the the liquid resin and the catalyst.

6. The system of claim 1, wherein the inlet is configured to be removable from the support after the liquid resin and the catalyst from the external pack transform into the solid.

7. The system of claim 1, wherein the longitudinal seam includes a plurality of tabs extending away from the body area when in use, and wherein the plurality of tabs are configured to be cut for removal of the flexible sleeve from the body area after use.

8. A method of forming a support for application to a body area, the method comprising:
providing the system of claim 1;
placing the flexible sleeve around the body area for application of a solid support;
attaching the inlet to the outlet;
breaking the first frangible seal and the second frangible seals to mix the liquid resin and catalyst together;
flowing the mixed liquid resin and catalyst into the second lumen of the lattice structure, wherein the mixed liquid resin and catalyst transforms into a solid in the second lumen such that the flexible sleeve hardens into the support for application to the body area; and
removing the inlet from the lattice structure after the lattice structure forms the solid support.

9. The method of claim 8, further comprising:
providing a predetermined color additive in the third chamber, wherein the color additive is a non-white color, and wherein the lattice structure is substantially transparent, such that during mixing and transformation, the lattice structure turns into a predetermined non-white color support.

10. The method of claim 8, further comprising:
cutting the longitudinal seam after the lattice structure forms a support to remove the support from the body area.

11. The method of claim 8, further comprising:
providing a removable plastic insert placed within the flexible sleeve to assist with placement of the flexible sleeve over the body area and removing the removable plastic insert prior to connecting the inlet and the outlet together.

12. The method of claim 8, further including the step of:
providing a retardant or an accelerant contained in the third chamber to adjust a curing time of the transformation of the liquid resin and catalyst into the solid.

13. A flexible sleeve to provide a support to a body area, the flexible sleeve comprising:
a network of flexible non-porous tubing interlaced at a plurality of junctions to form a lattice structure that defines a plurality of apertures configured to allow for a flow of air and water to the body area and to accommodate for unique contours of the body area, wherein the lattice structure comprises:
a bottom layer of the network of flexible non-porous tubing configured to contact the body area when in use;
a top layer of the network of flexible non-porous tubing;
a middle layer of the network of flexible non-porous tubing positioned between the bottom layer and the top layer and connected to the bottom layer and the top layer to form (i) a first lumen defined by the bottom layer and the middle layer, and (ii) a second lumen defined by the top layer and the middle layer, wherein a thickness of the top layer is greater than a thickness of the middle layer and a thickness of the bottom layer;
a thermo-resistant padding positioned in the first lumen, wherein the thermo-resistant padding comprises a flowable and injectable material that cures within the first lumen into a non-flowable solid material; and
a longitudinal seam in the network of flexible non-porous tubing extending from a first end of the lattice structure to a second end of the lattice structure, wherein the longitudinal seam includes the bottom layer, the middle layer, and the top layer, and wherein the longitudinal seam does not include the first lumen or the second lumen such that the longitudinal seam is void of both the thermo-resistant padding and a resinous material; and
an inlet in fluid communication with the second lumen of the lattice structure to permit the flow of fluids into and out of the network of flexible non-porous tubing.

14. The flexible sleeve of claim 13, wherein the thermo-resistant padding is sealed within the first lumen of the lattice structure.

15. The flexible sleeve of claim 13, wherein body area comprises a single joint.

16. The flexible sleeve of claim 13, wherein the longitudinal seam includes a plurality of tabs extending away from the body area when in use, and wherein the plurality of tabs are configured to be cut for removal of the flexible sleeve from the body area after use.

17. The flexible sleeve of claim 13, wherein the inlet is configured to be removable from the support.

\* \* \* \* \*